United States Patent [19]

Berg

[11] Patent Number: 4,471,297
[45] Date of Patent: Sep. 11, 1984

[54] MULTI-SAMPLE PARTICLE ANALYSIS APPARATUS AND METHOD

[75] Inventor: Robert H. Berg, Elmhurst, Ill.

[73] Assignee: Particle Data, Inc., Elmhurst, Ill.

[21] Appl. No.: 424,457

[22] Filed: Sep. 27, 1982

[51] Int. Cl.³ ............................................. G01N 27/00
[52] U.S. Cl. .................................. 324/71.1; 324/71.4; 422/64
[58] Field of Search ................. 324/71.1, 71.4; 377/10, 377/11, 12; 364/555; 422/63, 64

[56] References Cited

U.S. PATENT DOCUMENTS

| | | | |
|---|---|---|---|
| 3,124,172 | 3/1964 | Paxson, Jr. | 324/71.4 |
| 3,266,526 | 8/1966 | Berg | 138/103 |
| 3,554,037 | 1/1971 | Berg | 73/422 |
| 3,626,166 | 12/1971 | Berg | 235/151 |
| 3,648,160 | 3/1972 | Beaver | 324/71.4 |
| 3,763,429 | 10/1973 | Hoskins | 324/71 |
| 3,920,961 | 11/1975 | Berg | 235/92 |
| 4,296,373 | 10/1981 | Angel | 324/71 |

Primary Examiner—Michael J. Tokar
Assistant Examiner—Kevin D. O'Shea
Attorney, Agent, or Firm—Hill, Van Santen, Steadman & Simpson

[57] ABSTRACT

A suction chamber and at least one sample chamber are located in relatively shiftable operating adjacency. The suction chamber may have a plurality of orifices and the sample chamber a single port for selective registration with the orifices. On the other hand, the suction chamber may have a port or an orifice, and a plurality of sample chambers may have either respective ports or orifices, and the chambers mounted for relative shifting for effecting selective port/orifice registration. A sample depletion detector may be provided in association with the sample chamber. The sample chamber may have a minimum volume residual sample well for maintaining a filled system with the suction chamber to facilitate recurrent sample analyzing function.

20 Claims, 7 Drawing Figures

MULTI-SAMPLE PARTICLE ANALYSIS APPARATUS AND METHOD

This invention relates to improvements in particle analysis apparatus, and is more particularly concerned with novel apparatus and method for facilitating multi-sample particle analysis.

Common practice in the art of analyzing particles in a liquid carrier or electrolyte has been to draw the particles through a restricted orifice in the presence of an electrical current running between electrodes located at opposite sides of the orifice. Particles flowing through the sensing zone provided by the orifice modulate the electrical current. The electrical pulses thus generated are amplified and suitably recorded, totalized, visually observed on an oscilloscope, printed out by computer operation, and the like. Particle analyzing apparatus for accomplishing this is available under the trademark "ELZONE" from Particle Data, Inc., Elmhurst, Ill. That apparatus may embody circuitry and components represented by U.S. Pat. Nos. 3,626,166 and 3,920,961, which to any extent necessary are incorporated herein by reference.

In the prior arrangements, there is generally an orifice tube immersed in a container of particle bearing electrolyte, and the suspension is sucked through the orifice into the tube. This arrangement has at least two disadvantages, namely, that there is excessive electrical capacitance across the orifice due to the relatively large orifice tube area with oppositely charged liquid on opposite surfaces of the tube wall, and for each sample analysis, the immersed orifice tube and container have had to be separated and then the orifice tube rinsed and reimmersion effected with it, or another sample container or different orifice tube as might be required.

While the problem of excessive capacitance has been recognized and solved in a particular instance as disclosed in U.S. Pat. No. 3,554,037, the arrangement is limited to a fused orifice and pipeline sampling duct, wherein the assembly is fixed and limited to a single orifice usually for a very specialized use.

In an attempt to increase the particle analysis capability of a single suction system, arrangements as represented in U.S. Pat. Nos. 3,763,429 and 4,296,373 have been proposed wherein orifice tubes are selectively immersed in sample containing containers or beakers, but the disadvantages of orifice suction tubes immersed in the particle-containing electrolyte are inherent in these arrangements.

An important object of the present invention is to provide a new and improved apparatus and method for effecting multi-sample particle analysis which eliminates the problems inherent in orifice tube immersion and which provides a facility for quickly and efficiently performing successive particle analyses.

To this end, the present invention provides a multi-sample particle analysis apparatus, comprising suction chamber means and sample chamber means located in relatively shiftable operating adjacency, said suction chamber means and said sample chamber means having particle analysis orifice means and port means adapted for selective registration with one another, and means for relatively shifting said suction chamber means and said sample chamber means for effecting said selective registration.

The present invention also provides a method of effecting multi-sample particle analysis comprising locating suction chamber means and sample chamber means in relatively shiftable operating adjacency, said suction chamber means and said sample chamber means having particle analysis orifice means and port means adapted for selective registration with one another, and relatively shifting said suction chamber means and said sample chamber means and thereby effecting said selective registration of said orifice and port means.

Other objects, features and advantages of the invention will be readily apparent from the following description of representative embodiments thereof, taken in conjunction with the accompanying drawings, although variations and modifications may be effected without departing from the spirit and scope of the novel concepts embodied in the disclosure, and in which.

Figure 1:
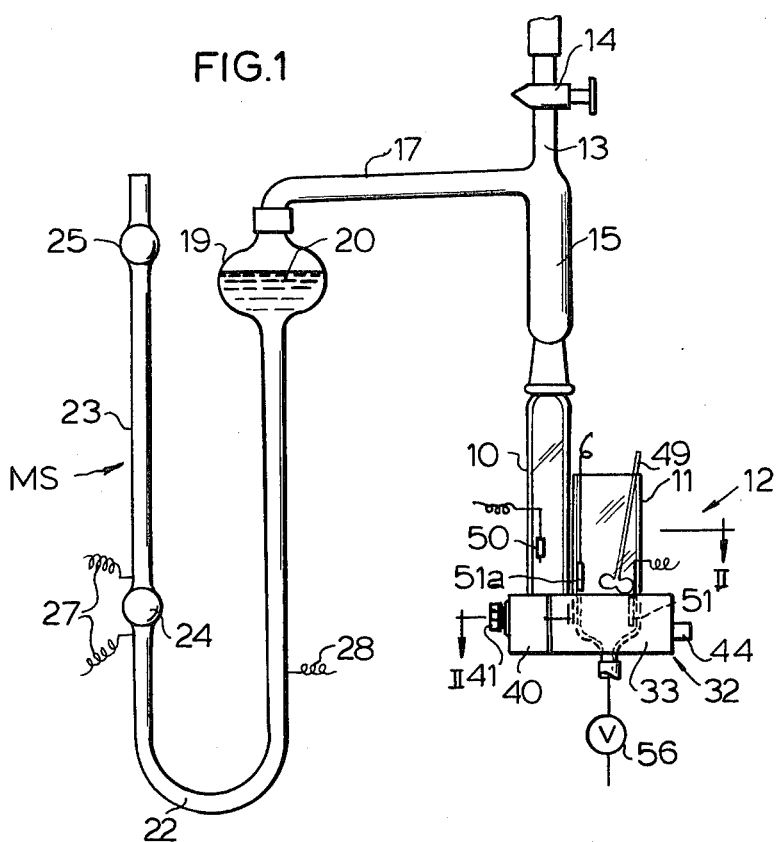
FIG. 1 is a schematic illustration of particle analysis apparatus embodying the present invention.
Figure 2:
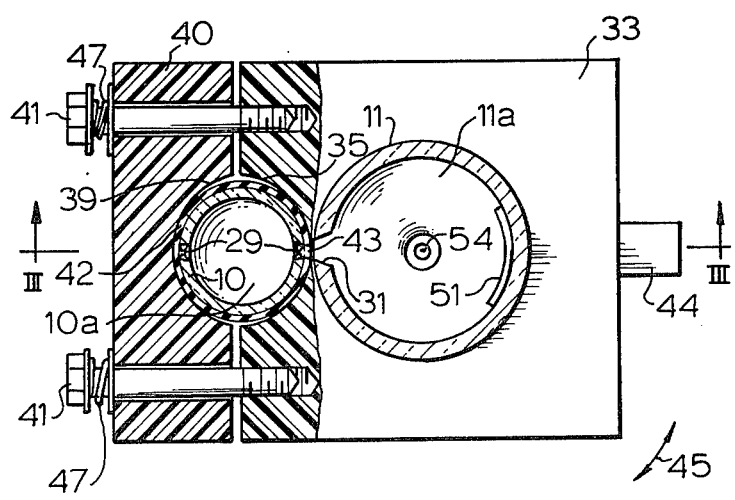
FIG. 2 is an enlarged sectional plan view taken substantially along the line II—II of FIG. 1.
Figure 3:
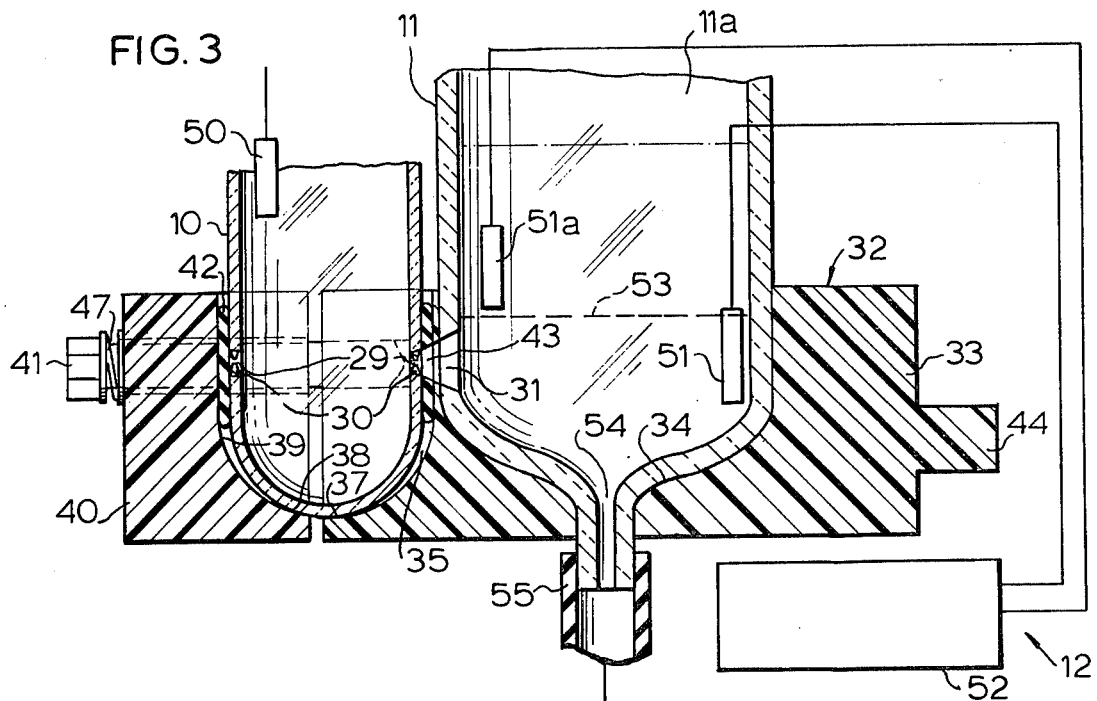
FIG. 3 is an additionally enlarged fragmentary vertical sectional view taken substantially along the line III—III of FIG. 2.

In the embodiment of the invention disclosed in FIGS. 1-3, suction chamber means in the form of a round orifice tube 10 defining a suction chamber 10a, and sample chamber means in the form of an open top, generally closed bottom tubular container 11 defining a sample chamber 11a, are located in relatively shiftable operating adjacency in a multi-sample particle analysis apparatus 12. By way of example, the suction chamber tube 10 is coupled to a metering siphon device MS on the order of that disclosed in the aforesaid U.S. Pat. No. 3,554,037, and comprising a suction head 13 having a valve 14 for controlling application of vacuum to a hollow body 15 in coupled communication with the top of the tube 10. Leading off from the top of the body 15 is a duct 17 connected by means of a coupling 18 to a reservoir enlargement 19 for a body of mercury 20 at the top of a mercury column tube 21 united by a goose neck 22 to the bottom of a vertical metering tube portion 23 having an intermediate reservoir enlargement 24 and an upper bulb reservoir 25. Electrical connections with evaluation apparatus are provided by means of probe electrodes 27. A grounding probe electrode 28 is located in the column 21.

The arrangement and functioning of the suction chamber means tube 10 and the sample chamber means receptacle or container 11 is such that particle analysis orifice means and port means are adapted for selective registration. In this instance, the suction chamber means tube 10 has a plurality of as many as desired particle analysis orifices, shown for simplicity as a pair of diametrically opposite orifices 29 provided by respective orifice disks 30 fixed in suitable apertures in the wall of the closed bottom tube 10. The orifice disks 30 may embody structure as disclosed in, and be mounted in the wall of the tube 10 in accordance with the method described in U.S. Pat. No. 3,266,526. The orifices 29 may be different or graduated sizes, so that a plurality of different particle size analyses may be effected from the same sample in the chamber 11a. In its lower end portion, the sample container 11 has a port 31 adapted for selective registration with the orifices 29.

Means are provided for supporting the container 11 relative to the tube 10 to permit rotary alignment of the port 31 with either selected one of the orifices 29. For this purpose, a base assembly 32 is provided comprising a member 33 providing a concave bottom socket 34 in which the lower end of the container 11 is supported with the port 31 opening into a laterally facing recess 35 within which the orificed lower end portion of the tube 10 is received for selective registration of the orifices 29 with the port 31. At the lower end of the recess 35, the base member 33 has a concave tube bottom supporting surface 37 which cooperates with a complementary tube bottom receiving surface 38 provided in the lower end of a cradle recess 39 complementary to the cradle recess 35 but formed in a base member 40 which is separably attached to the member 33 by means of bolts 41.

To provide a seal between the tube 10 and the container 11 about the aligned orifice 29 and the orifice 31, a sealing sleeve 42 snuggly receives the tube 10 slideably but in firm sealing engagement. To implement orifice realignment slidability of the tube surface engaged by the sleeve 42, such surface is desirably ground to as nearly as practicable true circularity in a centerless grinder, where the tube 10 is formed from glass.

In a preferred construction, the sleeve 42 is formed from a substantially self-lubricating plastic material, such as polytetrafluoroethylene. Thereby, the sleeve 42 is adapted to be slideably rotated about the tube 10, or the tube 10 may be slideably rotated within the sleeve 42, for selectively aligning either of the orifices 29 with a port 43 through the sleeve 41 aligned with and providing direct communication between the port 31 and the orifice 29 registered therewith.

Where the tube 10 is held in a relatively fixed operating position, the sample chamber means assembly is adapted to be rotated about the suction tube 10, and the sleeve is fixed to the member 33 with the ports 31 and 43 aligned. To this end, means such as a handle 44 on the member 33 is adapted to be manipulated for rotating the base 32 as indicated by the doubleheaded arrow 45 in FIG. 2 for attaining the selective registration. As the base 33 is rotated, carrying the container 11 and the sealing sleeve 42 with it, the orifice 29 registered with the port 31 is sealed off by the sleeve 41 and the other orifice 29 may be placed in registration with the port 32 after sufficient rotation of the member 31. To facilitate such rotary registration, the base member 38 is adapted to be backed off from a tube clamping and retaining relation to the base member 33. After the desired orifice/port registration is attained the screws 41 are retightened to draw the base members clampingly together and assure thorough sealing effect of the sleeve 42. To avoid damaging clamping pressure, cushioning take-up springs 47 are disposed between the heads of the bolts 41 and thrust washers 48.

In operation of the apparatus 12, a particle containing electrolyte sample is deposited in the sample chamber 11a, and if necessary, stirred as by means of a stirring device 49 (FIG. 1) to maintain the particles in suspension during analysis. Operation of the metering siphon device MS causes electrolyte and suspended particles to be drawn from the sample chamber 11a into the suction chamber 10a through the aligned orifice 29 and ports 31 and 43. The particles on passing through the orifice modulate an electrical current between an electrode 50 (FIG. 1) at the suction side of the orifice 29 and an electrode 51 (FIG. 3) located in the chamber 11a. Pulses caused by electrical current modulation by particles passing through the orifice 29 are transduced by the analyzing system represented at 52 in FIG. 3, and which may embody the systems, or elements thereof, exemplified in the aforesaid U.S. Pat. Nos. 3,626,166 and 3,920,961.

Automatic means for detecting substantial depletion of the sample being analyzed comprises a signaling electrode 51a (FIGS. 1-3) mounted within the chamber 11a at a desired low elevation. When the level of the suspension sample LS drops below the electrode 51a, as indicated by the horizontal dashed line 53, so that electrolytic action involving the electrodes 51 and 51a stops, the analyzing system 52 is signaled that the volume of sample available for analyzing has run out. Nevertheless, a small residual amount of the sample may remain in the bottom of the chamber 11a to maintain a fluid filled system with the chamber 10a in the suction orifice tube 10.

When it is desired to flush the sample chamber 11a, drain port 54 in the bottom of the container 11, and connected to a drain duct 55 under the control of a valve 56, may be opened.

Figure 4:
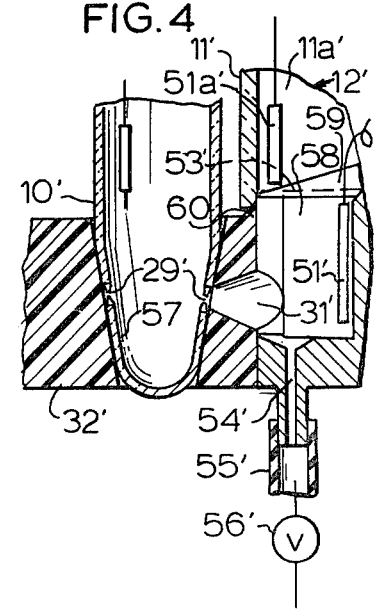
FIG. 4 is a fragmentary vertical sectional detail view showing a modified form embodying the invention.

In another desirable embodiment of the invention, apparatus 12' as shown in FIG. 4 may have an arrangement which avoids the need for a sealing member (such as 42) between the suction chamber means tube 10' and base member 32', as well as other attributes. To this end, the lower closed end portion of the tube 10' is of downwardly tapered form and accurately shaped to fit in sealing slideable engagement within an upwardly flaring complementary socket 57 in the member 32'. Either the base 32' carrying the container 11' may be rotatable about the tube 10', or the sample chamber tube 11' and the base 32' may remain stationary and the suction tube 10' adapted to be shifted about its axis, for aligning either selected orifice 29' with the port 31' which in this instance is formed in the base 32' and leads from a small volume well 58 formed in the base 32'. The well 58 is desirably of as small as practicable volume to contain a bare residual amount of sample to maintain a filled system through the port 31' and the suction tube chamber 10' but of small enough volume to accelerate clearing out residual sample through the suction tube 10' before starting analysis of the following sample charged into the chamber 11a'. Provision of the minimum volume well 58 may not be necessary for many particle analyzing operations, but there are some areas where it may be quite useful, such as, for example, in the biological disciplines where a substantially total countout may be highly desirable. To implement the minimum volume residual well 58, the base 32' is desirably provided with a base surface 59 which slopes toward and assures drainage of residual sample into the well 58. In addition, the lower end of the container 11' is open and engaged sealingly about an upwardly projecting boss 60 provided on the base 32' and having the sloping surface 59 facing upwardly thereon. In this instance, the electrode 51', which corresponds to the electrode 51 in FIG. 3, is located in the well 58. The depletion indicating electrode 51a', which corresponds to the electrode 51a in FIG. 3, is located as close as practicable adjacent to the top of the well 58, or may even be located in the well above the port 31' to detect when the level of the suspension sample drops below the horizontal dashed line 53'. For flushing the sample chamber 11a' as well as the well 58, the drain port 54' is located in the bottom of the well 58 and connected to drain duct 55' controlled by valve 56'. In other respects, the arrangement and operation of the apparatus 12' may be substantially the same as described for the apparatus 12.

Figure 6:
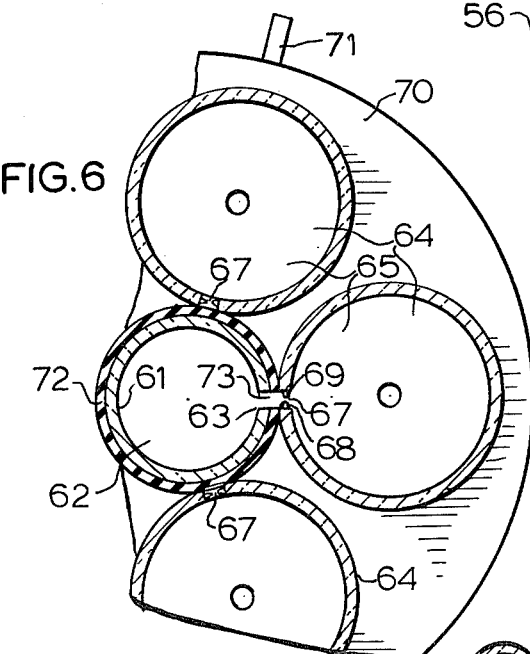
FIG. 6 is a fragmentary sectional plan view taken substantially along the line VI—VI of FIG. 5.
Figure 5:
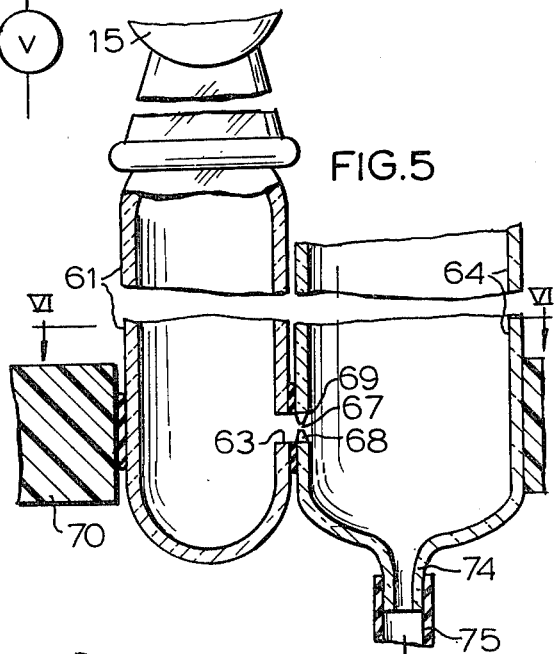
FIG. 5 is a fragmental vertical sectional detail view showing another modified embodiment of the invention.

In the embodiment depicted in FIGS. 5 and 6, a closed bottom, open top round suction tube 61 defining a suction chamber 62 and coupled with hollow vacuum body 15 has a single suction intake port 63. A plurality of sample tube containers 64 each providing a sample chamber 65, is mounted in relatively shiftable operating adjacency in a cluster about the suction tube 61. Each of the sample containers 64 has a particle analysis orifice 67 provided by an orifice disk 68 fixed in an aperture 69 in the wall of the tube, preferably in accordance with the teaching of U.S. Pat. No. 3,266,526.

The sample containers 64 are carried by means comprising a rotatable turntable 70 having thereon means 71 for effecting the rotation, in this instance in either rotary direction. Thereby, selective registration of the orifices 67 of the containers 64 with the port 63 is effected. Each of the orifices 67 may be of a different diameter for effecting different or graduated particle analysis in the apparatus. A sealing sleeve 72 fixed about the suction tube 61 has a port 73 aligned with the suction tube port 63 and the orifice 67 of any selected one of the sample containers 64 is adapted to be placed in registration with the port 63. The orifices 67 of the remaining containers 64 are maintained sealed by contact of the respective containers 64 with the sleeve 72 as shown in FIG. 6. At its lower end, each of the containers 64 may be provided with a nipple 74 to which is attached a drain duct 75 controlled by a valve 77. Particle analysis operation of the apparatus of FIGS. 5 and 6 may be substantially the same as described in connection with the apparatus of FIG. 1.

Figure 7:
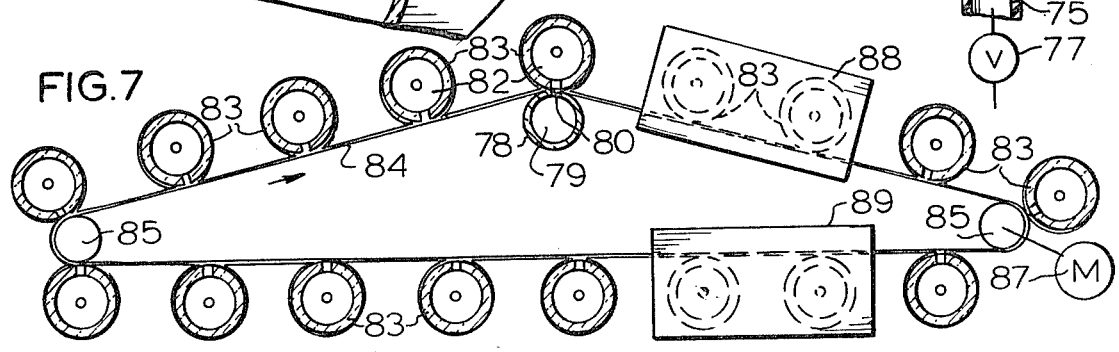
FIG. 7 is a more or less schematic sectional plan view of still another modified embodiment of the invention.

In FIG. 7 is shown an embodiment which is especially adapted for repetitive particle sample analysis. For this purpose a suction tube 78 has therein a suction chamber 79 and is provided with a particle analysis orifice 80 which is adapted to be selectively registered with a respective port 81 of any one of a plurality of sample chamber means tube containers 82 each of which has a sample receiving chamber 83. In this instance, the containers 82 are mounted at spaced intervals on an endless carrier 84, such as a belt which is adapted to be advanced by and about spaced capstans 85, one of which may be driven as by means of a stepping motor 87 to place the port 81 of any selected one of the sample chambers 83 provided by the containers 82 in registration with the orifice 80. As each of the containers 82 is brought into alignment with the suction tube 78, the sample to be analyzed is delivered into the chamber 82 of the container and the analyzing function then performed in customary manner. At completion of the analysis the belt 84 is advanced to bring another container 82 into sample analysis position and the used container 82 is advanced into a cleanout washer 88. Thence, the washed containers are advanced through a dryer 89 and are ready for reuse in the cyclical dwell and advance operation of the apparatus. At each orifice/port registration the belt 84 is adapted to provide a seal between the tube 78 and the container 82 about a clearance aperture in the belt aligned with the orifice 81.

It will be understood that variations and modifications may be effected without departing from the novel concepts of this invention.

I claim as my invention:

1. A multi-sample particle analysis apparatus, comprising:
   suction chamber means and sample chamber means adapted for relative shiftable side-by-side operating alignment;
   one of said suction chamber means and said sample chamber means having particle analysis orifice means and the other of said suction chamber means and sample chamber means having port means and said orifice means and said port means being adapted for selective registration with one another so that there is direct flow communication through the orifice means and port means from said sample chamber means into said suction chamber means;
   and means enabling relative shifting alignment of said suction chamber means and said sample chamber means for effecting said selective registration.

2. Apparatus according to claim 1, wherein said suction chamber means is in the form of a suction tube having said particle analysis orifice means, and said sample chamber means comprises a container structure having said port means.

3. Apparatus according to claim 1, wherein said suction chamber means is in the form of a suction tube having said port means, and said sample chamber means comprises container structure having said particle analysis orifice means.

4. Apparatus according to claim 1, including means sealing against leakage about the orifice means as registered with said port means.

5. Apparatus according to claim 4, wherein said sealing means comprises a plastic sealing bank engaged about said suction chamber means.

6. Apparatus according to claim 1, wherein said suction chamber means comprises a circular member having said port means, and said sample chamber means comprise a plurality of sample chambers contiguous to said member, and each sample chamber having a particle analysis orifice facing toward said member and selectively registerable with said port means.

7. Apparatus according to claim 6, wherein said shifting means comprises a turntable carrying said sample chambers.

8. Apparatus according to claim 1, wherein said suction chamber means comprises a stationary structure, said sample chamber means comprising a plurality of chamber members, said means for shifting comprises an endless carrier supporting said members, and means for moving said carrier for aligning said chamber members seriatim with said suction chamber means for effecting registration of said orifice means and said port means in flow-through relation.

9. Apparatus according to claim 8, including step and dwell driving means for said carrier.

10. Apparatus according to claim 1, wherein said sample chamber means comprises structure defining an upwardly flaring socket, and said suction chamber means comprises a tube having a tapered closed end complementary to and adapted to fit in sealing engagement within said socket.

11. Apparatus according to claim 1, wherein said sample chamber means comprises an upwardly extending tubular member defining a sample chamber, a base supporting said member and defining a bottom for said chamber sloping toward a small volume residual sample well adapted for side-by-side alignment with said suction chamber means, said orifice means and said port means communicating with said sample chamber through said well, and means for selectively flushing said well.

12. Apparatus according to claim 1, in combination with a particle analyzing system including a sample depletion signalling means associated with said sample chamber means.

13. A method of effecting multi-sample particle analysis, comprising:
locating suction chamber means and sample chamber means in relatively shiftable side-by-side operating alignment;
one of said suction chamber means and said sample chamber means having particle analysis orifice means and the other of said suction chamber means and sample chamber means having port means and said orifice means and said port means being adapted for selective registration with one another so that there is direct flow communication through the orifice means and port means from said sample chamber means into said suction chamber means;
and relatively shifting said suction chamber means and said sample chamber means for effecting said selective registration of said orifice means and said port means.

14. A method according to claim 13, which comprises maintaining one of said suction chamber means and sample chamber means stationary and relatively shifting the other of said suction chamber means and sample chamber means.

15. A method according to claim 14, comprising maintaining said suction chamber means stationary and shifting said sample chamber means relative to said suction chamber means.

16. A method according to claim 15, which comprises effecting said shifting cyclically, and in each cycle washing and drying said sample chamber means.

17. A method according to claim 13, which comprises providing a sample depletion signal upon run-out of sample in said sample chamber means.

18. A method according to claim 13, which comprises maintaining a residual volume of sample in said sample chamber means after a sampling procedure, so that a liquid filled relationship persists at the port/orifice registration area of said sample chamber means.

19. A method according to claim 13, wherein said suction chamber means comprises a circular chamber member and said sample chamber means comprises a cluster of sample chambers in contiguity to said member, and said relatively shifting comprising relatively displacing said sample chambers about said member.

20. A method according to claim 13, wherein said suction chamber means comprises a stationary member, and said sample chamber means comprises a set of sample chamber on an endless carrier, and moving said carrier to effect said relatively shifting.

* * * * *